(12) United States Patent
Lee et al.

(10) Patent No.: US 8,302,464 B2
(45) Date of Patent: Nov. 6, 2012

(54) AUTOMATIC SEQUENTIAL SAMPLER FOR ROOF-TOP RUNOFF OF RAINWATER

(75) Inventors: Bong Joo Lee, Daejeon (KR); Yong Cheol Kim, Daejeon (KR); Sang Ho Moon, Daejeon (KR); Ki Hwa Park, Daejeon (KR); Byoung Woo Yum, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 425 days.

(21) Appl. No.: 12/557,894

(22) Filed: Sep. 11, 2009

(65) Prior Publication Data

US 2010/0089179 A1   Apr. 15, 2010

(30) Foreign Application Priority Data

Oct. 15, 2008   (KR) .................. 10-2008-0101264

(51) Int. Cl.
*G01N 1/20* (2006.01)

(52) U.S. Cl. ............... 73/64.56; 73/863.01; 73/863.02; 73/864.63

(58) Field of Classification Search ............... 73/863.01, 73/64.56, 864.63
See application file for complete search history.

(56) References Cited

U.S. PATENT DOCUMENTS

| 4,732,037 A | 3/1988 | Daube, Jr. et al. |
| 7,008,529 B2 * | 3/2006 | Nakanishi et al. ............ 210/98 |
| 2001/0030161 A1 | 10/2001 | Hosoya |
| 2008/0105306 A1 | 5/2008 | Takai |

* cited by examiner

*Primary Examiner* — Hezron E Williams
*Assistant Examiner* — Paul West
(74) *Attorney, Agent, or Firm* — Rabin & Berdo, P.C.

(57) ABSTRACT

There is provided an automatic sequential sampler for rooftop runoff of rainwater, which comprises: a sensing part, a controlling part and a sampling part, and more particularly, which takes samples of rainwater, at regular intervals, by sensing whether it rains and controlling the rotation and stop of a sample bottle shelf in the sampling part, using a timer and a counter.

7 Claims, 3 Drawing Sheets

AUTOMATIC SEQUENTIAL SAMPLER FOR ROOF-TOP RUNOFF OF RAINWATER

CROSS-REFERENCE TO RELATED PATENT APPLICATION

This application claims the benefit of Korean Patent Application No. 10-2008-0101264, filed Oct. 15, 2008 in the Korean Intellectual Property Office, the disclosure of which is incorporated herein in its entirety by reference.

BACKGROUND

1. Field of the Invention

The present invention relates to an automatic sequential sampler for roof-top runoff of rainwater, to easily sample rainwater at regular intervals.

2. Description of the Related Art

With concern about lack of water resources in the future, efforts to develop new water resources have been actively made and the reuse of rainwater as alternative water resources has been newly understood. Rainwater is collected through catchments on the roofs of buildings, greenhouses or the like and is stored in reservoir facilities, to be reused for various purposes. To increase the use of rainwater, it needs to control and maintain the high-level quality of rainwater. To this end, it is necessary to conduct research on the first flush phenomenon of rainwater collected in the catchments. In general, rainwater at the early stage of rainfall shows relatively more contamination properties, compared with rainwater at the later stage of rainfall. This is known as the first flush phenomenon of rainwater collected in the catchments. To accurately analyze variations of rainwater qualities with time, it needs to collect rainwater, at regular intervals, from the point of time when rainfall starts to the point of time when rainfall stops. However, a conventional method of collecting rainwater has a problem in that a human has to collect rainwater at regular intervals.

SUMMARY

The present invention has been made to solve the above problems and it is an object of the present invention to develop the technology for sequentially sampling rainwater at regular intervals, by automatically sensing whether it rains.

The present invention provides an automatic sequential sampler for roof-top runoff of rainwater, comprising: a sensing part; a controlling part; and a sampling part, wherein, in the sensing part, a sensor senses rainfall only when rainfall reaches a certain level or higher and sends a signal thereof to the controlling part; the controlling part controls the sampling part by using a counter and a timer; and the sampling part controls two motors (one is for rotation, the other is for stop) thereof so that a sample bottle shelf rotates, at a certain angle, at a set time, whereby it is possible to automatically collect rainwater for sampling when it continuously rains and to easily and sequentially take rainwater samples at set times, and therefore, an operator does not need to collect rainwater for samples at each time.

The other objects and advantages of the present invention will be described below and become more apparent by describing exemplary embodiments thereof. Further, the objects and advantages of the present invention will be achieved by elements and a combination of the elements disclosed in the claims.

According to an aspect of the present invention, there is provided an automatic sequential sampler for roof-top runoff of rainwater, comprising: a collecting part for collecting rainwater, one end of which is divided into a first pipe and a second pipe; a sensing part operatively connected to the first pipe; a first valve positioned at a certain part of the second pipe; a sampling part for sampling rainwater through a supply pipe with one end operatively connected to one end of the second pipe and the other end inserted into the sampling part; and a controlling part installed in the sampling part and electrically connected to the sensing part.

BRIEF DESCRIPTION OF THE DRAWINGS

The above and other features and advantages of the present invention will become more apparent by describing in detail exemplary embodiments thereof with reference to the attached drawings in which.

Figure 1:
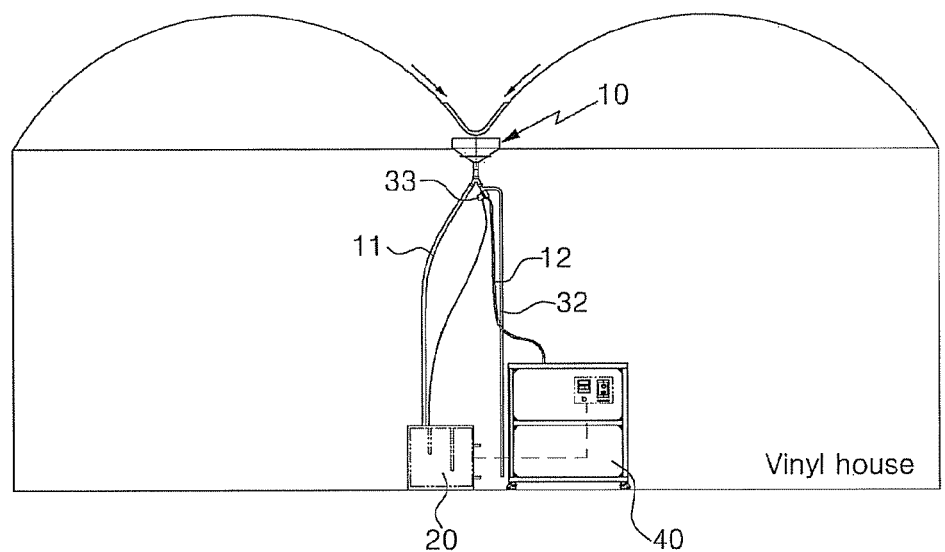
FIG. 1 is a front view illustrating the application of an automatic sequential sampler for roof-top runoff of rainwater according to an embodiment of the present invention.

| [Brief description of reference numbers of major elements] | |
|---|---|
| 10: | collecting part |
| 11: | first pipe |
| 12: | second pipe |
| 20: | sensing part |
| 21: | first electrode |
| 22: | second electrode |
| 23, 23': | outlet |
| 31: | supply pipe |
| 32: | bypass pipe |
| 33: | first valve |
| 40: | sampling part |
| 50: | sampler |
| 51: | support shaft |
| 52: | support plate |
| 53: | holder |
| 54: | sample bottle |
| 55: | protruding piece |
| 60: | proximity sensor |
| 61: | stand |
| 70: | motor |
| 71: | brake motor |
| 72: | power transmission unit |

DETAILED DESCRIPTION

Before exemplary embodiments of the present invention are described in detail, it will be understood that, detailed constitution and arrangements of elements described in the detailed description or illustrated in the drawings should not be construed as limiting the application of the invention. The invention may be embodied in many alternate forms and performed in various methods. The terms or words to describe the direction of an apparatus or element (for example, "front", "back", "up", "down", "top", "bottom", "left", "right" and "lateral", among others) are used to simplify the description of the invention. It will be, therefore, understood that these terms do not mean that the relevant apparatus or element shall be only in the specific direction. It will be also understood that, the terms, such as "first" or "second", are used for clarification in the detailed description and claims and therefore, the terms should not be construed as indicating any relative importance, intent or meaning.

The present invention will now be described more fully hereinafter with reference to the accompanying drawings, in which preferred embodiments of the invention are shown. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Accordingly, while example embodiments of the present invention are capable of various modifications and alternative forms, embodiments of the present invention are shown by way of example in the drawings and will herein be described in detail. It should be understood, however, that there is no intent to limit example embodiments of the invention to the particular forms disclosed, but on the contrary, example embodiments of the invention are to cover all modifications, equivalents, and alternatives falling within the scope of the invention.

As used herein, the singular forms "a", "an" and "the" are intended to include the plural forms as well, unless the context clearly indicates otherwise.

An automatic sequential sampler for roof-top runoff of rainwater according to a preferred embodiment of the present invention will be described with reference to FIGS. 1 through 5.

As illustrated, the automatic sequential sampler for roof-top runoff of rainwater comprises: a collecting part 10, a first pipe 11, a second pipe 12, a sensing part 20, a supply part 31, a bypass pipe 32, a first valve 33, a sampling part 40, a sampler 50, a motor 70, a brake motor 71, a proximity sensor 60, and a controlling part 80.

The collecting part 10 is in the shape of a funnel with a wider opening at an upper end and a narrower opening at a lower end. The lower end having a relatively narrower diameter is divided into the first pipe 11 and the second pipe 12.

The collecting part 10 collects rainwater and allows the roof-top runoff of rainwater to flow into both of the first and second pipes 11 and 12. However, since the first valve 33 (to be described later) connected to one end of the second pipe 12 is usually in an OFF-state, the rainwater collected in the collecting part 10 flows into the first pipe 11.

The second pipe 12 further includes the bypass pipe 32 which is downwardly divided from a front end of the first valve 33 connected to the second pipe 12.

Figure 2:
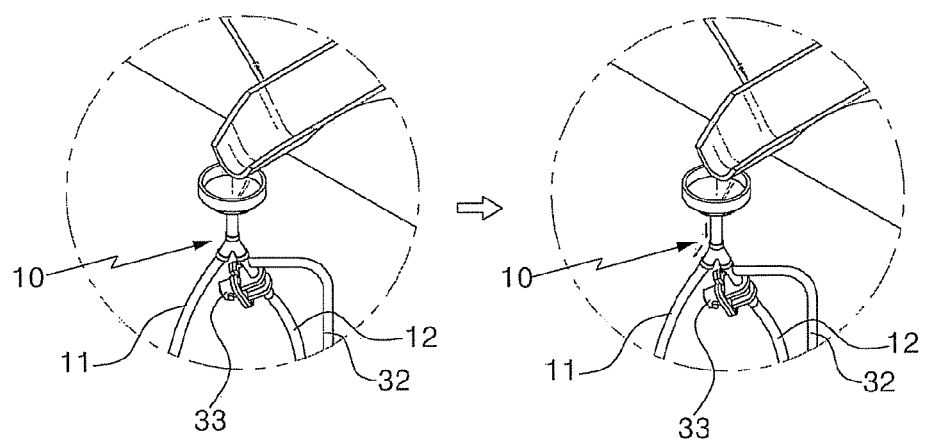
FIG. 2 is a perspective view illustrating a collecting part according to the present invention.
Figure 3:
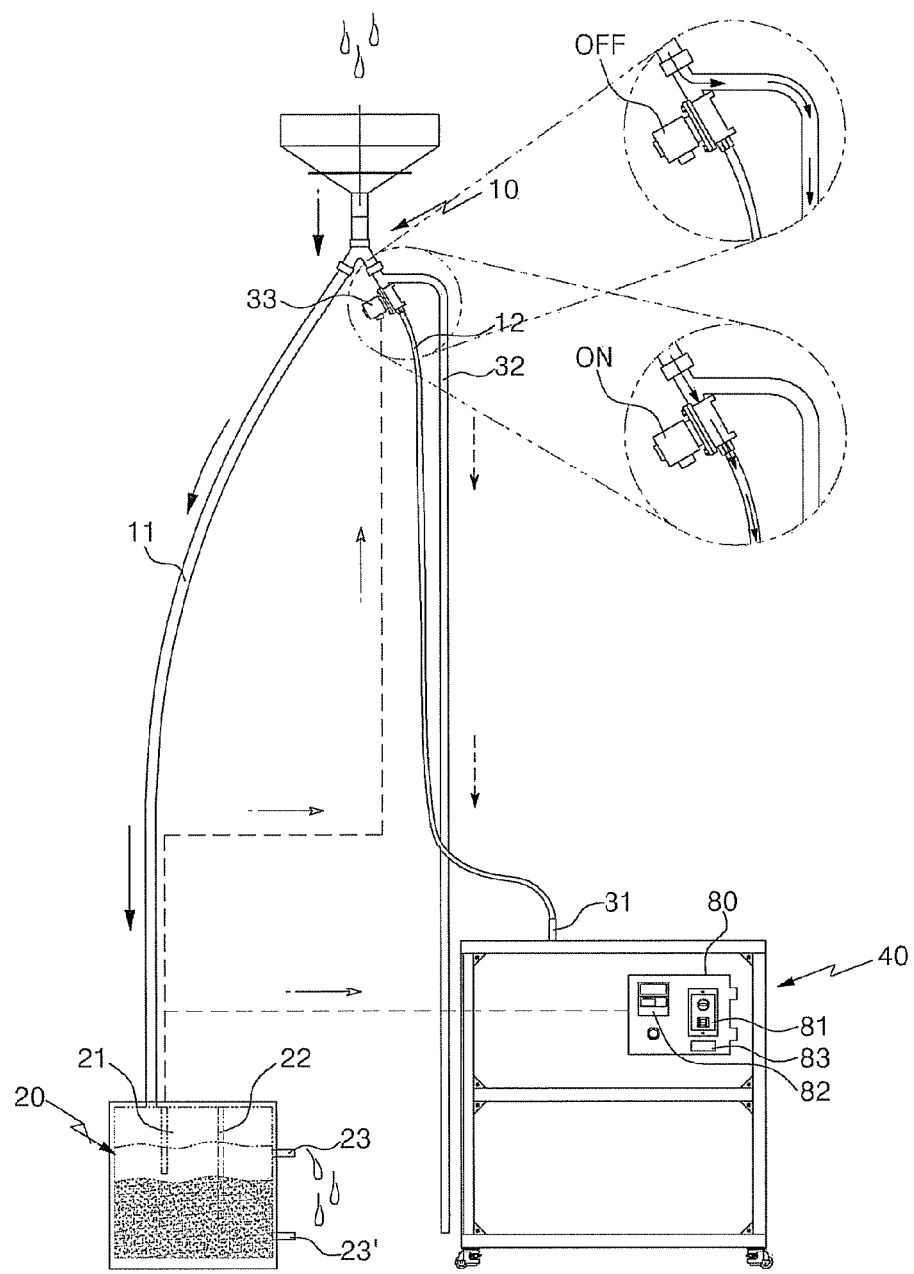
FIG. 3 is a front view illustrating the automatic sequential sampler for roof-top runoff of rainwater according to the embodiment of the present invention.
Figure 4:
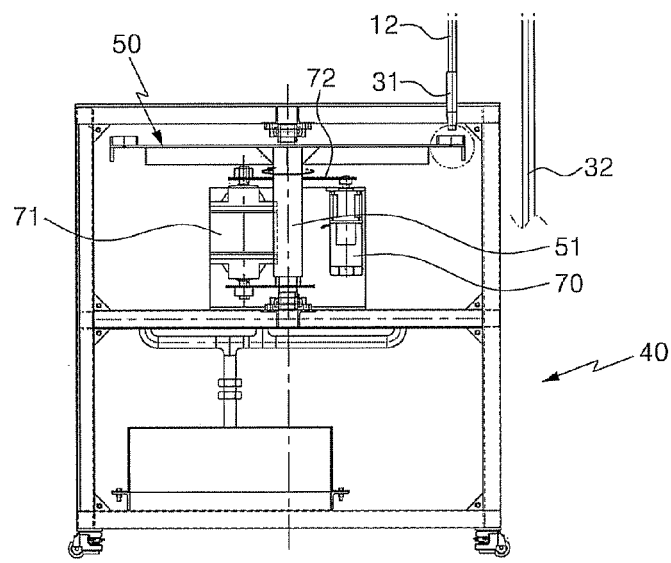
FIG. 4 is a front view illustrating an inside of the automatic sequential sampler for roof-top runoff of rainwater according to the embodiment of the present invention.

As illustrated in FIGS. 1 through 3, the first and second pipes 11 and 12 of the collecting part 10 are divided in the shape of ∧. The bypass pipe 32 is bent in the shape of ¬ from the front end of the first valve 33 of the second pipe 12, and one end of the bypass pipe 32 is toward the surface of land.

(Of course, when the automatic sequential sampler for roof-top runoff of rainwater does not sample rainwater or it is not appropriate to sample rainwater because the amount of rainfall is small and the bypass pipe has the bypass constitution capable of discharging a small amount of rainwater received in the collecting part 10 outside, the shape of the bypass pipe and the shape in which the first and second pipes are divided may vary according to embodiments of a user.)

During the first valve 33 is in the OFF-state, the rainwater flowing from the collecting part 10 flows into the sensing part 20 and the surface of land through the first pipe 11 and the bypass pipe 32, respectively.

However, when the sensing part 20 (to be described later) operatively connected to the end of the first pipe 11 generates a signal and the first valve 33 is converted from the OFF-state to an ON-state by the signal, the rainwater that has been flown into the first pipe 11 and the bypass pipe 32 flows into the first pipe 11 and the second pipe 12.

The sensing part 20 is operatively connected to one end of the first pipe 11 and is hollow. A plurality of electrodes, i.e., a first electrode 21 and a second electrode 22, hang down from an upper end of an inner circumferential surface of the sensing part 20. The first electrode 21 and the second electrode 22 are structured to be different from each other in length. That is, the length of the second electrode 22 is relatively longer than that of the first electrode 21, or the length of the first electrode 21 is relatively longer than that of the second electrode 22. (Depending on the user's selection, the sensing part 20 may be replaced by a water level controller for controlling a fluid so as not to be below a certain level.)

In the present invention, for clarification, the length of the first electrode 21 is shorter than that of the second electrode 22. In other words, since the second electrode 22 is longer in length, this means that one end of the second electrode 22 is closer to the bottom of the sensing part 20.

Since the first valve 33 is usually in the OFF-state, the rainwater flowing from the collecting part 10 flows into the first pipe 11 and the bypass pipe 32, respectively. Then, some of the rainwater is discharged to the surface of land through the bypass pipe 32 and some of the rainwater fills the sensing part 20 through the first pipe 11.

When the rainwater fills from the bottom of the sensing part 20 and reaches a certain level, the rainwater first contacts with the second electrode 22 which is longer in length, among the plurality of electrodes. When the rainwater continuously fills by a lot of rain and the rainwater level goes up, it contacts with the first electrode 21 in addition to the second electrode 22.

As described above, when the level of the rainwater filling the sensing part 20 reaches the certain level and contacts with both of the first and second electrodes 21 and 22, the sensing part 20 generates a signal to the first valve 33 electrically connected to the sensing part 20. The first valve 33 receiving the signal is switched from the OFF-state to the ON-state, so that the rainwater that has been flown into the bypass pipe 32 flows into the second pipe 12.

In other words, when the amount of rainfall is small, the automatic sequential sampler for roof-top runoff of rainwater is structured so as not to be operated, based on the plurality of electrodes of the sensing part 20, thereby preventing the collector from being unnecessarily driven. Only when the amount of rainfall is sufficient so that the rainwater contacts with both of the electrodes, the automatic sequential sampler for roof-top runoff of rainwater is structured so as to be operated.

Further, a plurality of outlets 23, 23' operatively connecting the inside/outside of the sensing part 20 is formed at the outer circumference of the sensing part 20. The outlet 23' is positioned at the lowest end of the outer circumference of the sensing part 20. After the automatic sequential sampler for roof-top runoff of rainwater is operated or when it is not used, the outlet 23' discharges the rainwater remaining inside the sensing part 20 outside. To the contrary, the outlet 23 is formed at the most upper end of the outer circumference of the sensing part 20. When the automatic sequential sampler for roof-top runoff of rainwater is operated and the level of the rainwater rises so that the rainwater contacts with both of the first and second electrodes 21 and 22, the outlet 23 discharges the rainwater outside, to prevent the rainwater from continuously and unnecessarily filling the sensing part 20.

The first valve 33 is positioned at the second pipe 12 of the collecting part 10. The first valve 33 is positioned so as to be close to the point at which one end of the collecting part 10 is divided into the first and second pipes 11 and 12.

As mentioned in the description of the sensing part 20, the first valve 33 is electrically connected to the sensing part 20 and is in the ON-state only when the signal from the sensing part 20 is generated, so that the rainwater flowing from the collecting part 10 is delivered into the sampling part 40 through the supply pipe 31. Further, a solenoid valve is used as the first valve 33.

The sampling part 40 is in the shape of an empty square box. One end of the supply pipe 31 with the other end operatively connected to one end of the second pipe 12 is inserted into the sampling part 40. The sampler 50 (to be described later) and various constituent elements are installed inside the sampling part 40. (The shape of the sampling part 40 may vary according to the user's selection.)

The sampler 50 is installed inside the sampling part 40. The sampler 50 comprises: a support shaft 51 installed in a perpendicular direction to the surface of land in the sampling part 40; a support plate 52 fixed on an upper end of the support shaft 51 and installed around the support shaft 51 in a horizontal direction to the surface of land; a number of holders 53 formed, along with the circumferential surface of the support plate 52 (i.e., forming a circle at the edge of the support plate 52); and a number of sample bottles 54 each positioned to be inserted in an upper end of the holder 53.

Each of the sample bottles 54 is in the shape of a cylinder with an opening at its upper end and a hollow inside. Each of the holders 53 securely holds the sample bottle 54 so as to be stable.

Figure 5:
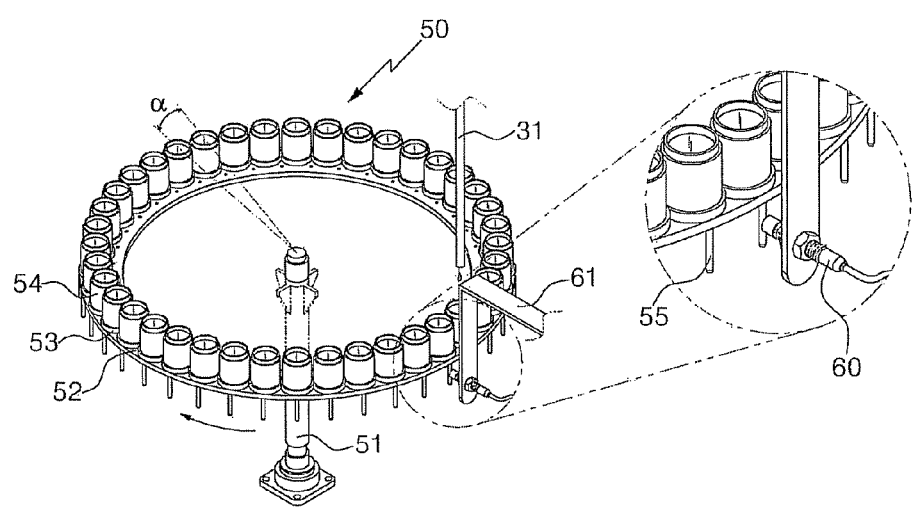
FIG. 5 is a perspective view illustrating a sampler in the automatic sequential sampler for roof-top runoff of rainwater according to the embodiment of the present invention.

(As illustrated in FIG. 5, for example, forty (40) sample bottles 54 are used in the embodiment of the present invention.)

One of the sample bottles 54 is positioned to correspond to and be spaced apart from a lower end of the supply pipe 31 (inserted into the sampling part 40) at a certain space, so that the rainwater flowing from the supply pipe 31 is collected in the one sample bottle 54.

In addition to the sampler 50, the motor 70 and the brake motor 71 are installed in the sampling part 40. The motor 70 and the brake motor 71 are the constituent elements to rotate the support shaft 51.

One end of the motor 70 and one end of the brake motor 71 are connected to each other, to transmit power by the power transmission unit 72 (for example, chain, belt, or the like). A rotation force of the motor 70 is transmitted to the brake motor 71 and the other end of the brake motor 71 receiving the rotation force of the motor 70 is connected to a lower end of the support shaft 51, thereby transmitting power by the power transmission unit 72 and consequently rotating the support shaft 51.

The controlling part 80 is electrically connected to the motor 70 and the brake motor 71, controlling the rotation of the motor 70 and brake motor 71. The controlling part 80 comprises: a speed controller 81, a counter 82 and a timer 83.

The motor 70 is driven when the first valve 33 is in the ON-state, based on the signal generated from the sensing part 20. The motor 70 being driven transfers the rotation force to the brake motor 71 so as to be operated.

The speed controller 81 controls a rotation speed of the motor 70. The timer 83 is used in order that signals are transmitted at set times predetermined by the user, to the brake motor 71 to be operated. The brake motor 71 is another motor which is like the motor 70 but further includes a brake device. When a control signal or an electric signal is input, a brake (not shown) inside the brake motor 71 is made to be either operated or to the contrary cancelled.

That is, when one end of the brake motor 71 receives the rotation force of the motor 70, the brake (not shown) inside the brake motor 71 operates so as not to transfer the rotation force to the other end of the brake motor 71. Then, when the signals are received at the set times by the timer 83, the operation of the brake (not shown) is cancelled so as to transfer the rotation force to the other end of the brake motor 71, thereby rotating, at a certain angle α, the support shaft 51 connected to the other end of the brake motor 71 by the power transmission unit 72. After rotating the support shaft 51 at the certain angle α, the brake (not shown) inside the brake motor 71 operates so that the rotation force should not be transferred to the support shaft 51.

The certain angle α, at which the support shaft 51 is rotated, is the angle to sequentially position the sample bottles 54 under the lower end of the supply pipe 31 inserted into the sampling part 40. (Therefore, the certain angle α may vary according to the number of the sample bottles 54.) Since the support shaft 51 rotates, each of the sample bottles 54 is able to separately collect the rainwater at the set times.

The counter 82 is electrically connected to the timer 83, to count the number of times of rotation whenever the brake motor 71 is operated to rotate the support shaft 51. As illustrated in FIG. 5, when the number of the sample bottles 54 is forty (40), the maximum counting number will be forty (40). (Thereafter, when the rainwater is completely collected in all of the sample bottles 54, all of the aforementioned constituent elements stop operating.) The controlling part 80 is to be installed outside the sampling part 40, to be recognized and easily operated outside. However, the controlling part 80 may be installed inside the sampling part 40 at the user's selection. In this case, the outer circumferential surface of the sampling part 40 may be structured so as to be opened and closed.

The proximity sensor 60 is installed at one end of a stand 61 inside the sampling part 40. One end of the proximity sensor 60 is toward the sampler 50. A number of protruding pieces 55 protruding downward are formed on the lower end of the support plate 52 of the sampler at all portions where the sample bottles 54 are positioned. The proximity sensor 60 is positioned to be close to one of the protruding pieces 55.

To describe in more detail, the proximity sensor 60 has to be positioned proximately to the protruding piece 55 under the lower end of the sample bottle 54 containing the rainwater supplied from the supply pipe 31.

That is, since the supply pipe 31 supplies the rainwater through its lower end at a fixed position and the support shaft 51 rotates at the certain angle α to allow a number of the sample bottles 54 to sequentially receive the rainwater supplied from the supply pipe 31 at set times, the proximity sensor 60 detects whether each of the sample bottles 54 is operatively positioned exactly under the fixed supply pipe 31.

(The term "set times" means the time when each sample bottle 54 receives the rainwater. Therefore, the set time may be optionally set by the user or it may vary depending on a speed at which the rainwater is supplied.)

The automatic sequential sampler for roof-top runoff of rainwater according to the present invention, which has the above-described constitution and operation, may be used to sample water of a river, runoff on the surface of a road or the surface of the earth in addition to rainwater, by the user's selection.

As described above, when it rains continuously, the automatic sequential sampler for roof-top runoff of rainwater according to the present invention senses rainfall and automatically operates, thereby sequentially sampling rainwater.

Furthermore, the automatic sequential sampler for roof-top runoff of rainwater automatically and easily takes samples of rainwater, by times, thereby improving accuracy in analyzing the collected rainwater.

Furthermore, an operator does not need to directly take samples of rainwater periodically, thereby reducing labor and material costs.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An automatic sequential sampler for roof-top runoff of rainwater, comprising:
   a collecting part for collecting rainwater, with one end divided into a first pipe and a second pipe;
   a sensing part operatively connected to the first pipe;
   a first valve positioned at a certain position of the second pipe and electrically connected to the sensing part;
   a sampling part for sampling the rainwater, by receiving the rainwater flowing through a supply pipe with one end operatively connected to one end of the second pipe and the other end inserted into the sampling part; and
   a controlling part installed in the sampling part and electrically connected to the sensing part;
   wherein the second pipe further includes a bypass pipe being divided from a front end of the first valve and being toward the surface of land, wherein when the first valve is in an ON-state, the rainwater flows through the second pipe but when the first valve is in an OFF-state, the rainwater flowing through the collecting part is bypassed to flow into the surface of land by the bypass pipe; and
   wherein the sampling part includes a sampler comprising a support shaft, a support plate connected to one end of the support shaft, a number of holders formed, along with a circumference of the support plate, and a number of sample bottles respectively positioned at the holders, wherein one of the sample bottles is correspondingly positioned to be spaced apart, at a certain distance, from a lower end of the supply pipe of the sampling part.

2. The sequential sampler of claim 1, wherein the sensing part includes a first electrode and a second electrode being different from each other in length and hanging down from an upper portion of an inner circumferential surface of the sensing part, and when the rainwater filling the sensing part contacts with both of the first and second electrodes, the sensing part generates a signal, so that the first valve is switched from the OFF-state to the ON-state, to allow the rainwater of the collecting part to flow into the sampling part, wherein the first valve uses a solenoid valve.

3. The sequential sampler of claim 1, wherein the sensing part includes a plurality of outlets respectively formed at upper and lower ends of an outer circumference of the sensing part, wherein, when the amount of rainfall is small, the outlet discharges the rainwater remaining in the sensing part outside, and when the amount of rainfall is large, the outlet discharges the rainwater in the sensing part outside so that the rainwater reaches a certain level so as to contact with both of a first electrode and a second electrode and so as not to overflow from the sensing part.

4. The sequential sampler of claim 1, wherein the sampler comprises: a number of protruding pieces and a proximity sensor, wherein the protruding pieces are formed at a bottom of the support plate, each protruding piece is positioned at the position where each sample bottle is placed, and the proximity sensor is positioned proximately to the protruding piece of the sample bottle correspondingly positioned at the supply pipe, thereby detecting whether the rainwater flowing from the supply pipe is accurately collected in the sample bottle and whether the sample bottle is positioned to correspond to the lower end of the supply pipe.

5. The sequential sampler of claim 1, wherein the sampling part further includes a motor and a brake motor, wherein one end of the brake motor is connected to the motor so that power is transmitted by a power transmission unit and the other end of the brake motor is connected to the support shaft so that power is transmitted by the power transmission unit, thereby rotating the support shaft.

6. The sequential sampler of claim 1, wherein the controlling part comprises: a speed controller, a counter and a timer and operates a motor and a brake motor based on a signal generated from the sensing part, wherein the speed controller controls a rotation speed of the motor, the timer controls the brake motor to be operated at regular intervals so that the support shaft is regularly rotated at a certain angle at set times (at the regular intervals) by the brake motor, thereby sequentially rotating the number of sample bottles, one by one, to receive the rainwater at the set times (at the regular intervals), and
   the counter displays the number of times of rotation of the support shaft to be recognized outside.

7. The sequential sampler of claim 6, wherein the controlling part controls the operation of the sequential sampler to automatically stop when sampling is completed by collecting the rainwater in each of the number of sample bottles.

* * * * *